United States Patent [19]
Thornton et al.

[11] Patent Number: 5,634,930
[45] Date of Patent: *Jun. 3, 1997

[54] CLIP APPLICATOR SYSTEM

[75] Inventors: Curtis W. Thornton, Cary; Thomas W. Ruckdeschel, Apex; Elise P. Speaks, Cary, all of N.C.

[73] Assignee: Pilling Weck Incorporated, Research Triangle Park, N.C.

[*] Notice: The portion of the term of this patent subsequent to Dec. 17, 2013, has been disclaimed.

[21] Appl. No.: 405,449

[22] Filed: Mar. 14, 1995

Related U.S. Application Data

[63] Continuation of Ser. No. 999,437, Dec. 31, 1992, abandoned.

[51] Int. Cl.$^6$ ............................................. A61B 17/10
[52] U.S. Cl. ........................... 606/143; 606/142; 606/139
[58] Field of Search .............................. 606/139, 142, 606/143, 174; 227/91

[56] References Cited

U.S. PATENT DOCUMENTS

| | | |
|---|---|---|
| Re. 28,932 | 8/1976 | Noiles et al. . |
| D. 305,064 | 12/1989 | Mulhanser et al. . |
| 2,296,493 | 9/1942 | Bernstein . |
| 3,404,457 | 10/1968 | Swanstrom, Sr. ............... 606/174 |
| 3,675,688 | 7/1972 | Bryan et al. . |
| 4,196,836 | 4/1980 | Becht . |
| 4,246,903 | 1/1981 | Larkin . |
| 4,296,751 | 10/1981 | Blake, III et al. . |
| 4,372,295 | 2/1983 | Heckele . |
| 4,496,090 | 1/1985 | Crevier et al. . |
| 4,509,518 | 4/1985 | McGarry et al. . |
| 4,532,925 | 8/1985 | Blake, III . |
| 4,550,715 | 11/1985 | Santangelo et al. . |
| 4,562,839 | 1/1986 | Blake, III et al. . |
| 4,598,711 | 7/1986 | Deniega . |
| 4,616,650 | 10/1986 | Green et al. . |
| 4,656,999 | 4/1987 | Storz . |
| 4,662,373 | 5/1987 | Montgomery et al. . |
| 4,691,853 | 9/1987 | Storace . |
| 4,712,549 | 12/1987 | Peters et al. . |
| 4,759,364 | 7/1988 | Boebel . |
| 4,850,355 | 7/1989 | Brooks et al. . |
| 5,000,745 | 3/1991 | Guest et al. . |
| 5,009,391 | 4/1991 | Steingerwald . |
| 5,030,226 | 7/1991 | Green et al. . |
| 5,047,038 | 9/1991 | Peters et al. . |
| 5,049,152 | 9/1991 | Simon et al. . |
| 5,059,201 | 10/1991 | Asnis . |
| 5,084,057 | 1/1992 | Green et al. . |
| 5,100,420 | 3/1992 | Green et al. . |
| 5,104,394 | 4/1992 | Knoepfler . |
| 5,104,395 | 4/1992 | Thronton et al. . |
| 5,112,343 | 5/1992 | Thornton . |
| 5,156,608 | 10/1992 | Troidl et al. . |
| 5,163,945 | 11/1992 | Ortiz et al. . |
| 5,171,247 | 12/1992 | Hughett et al. . |
| 5,171,250 | 12/1992 | Yoon . |
| 5,403,327 | 4/1995 | Thornton et al. ............... 606/143 |
| 5,433,725 | 7/1995 | Christian et al. ............... 606/207 |

FOREIGN PATENT DOCUMENTS

| | | |
|---|---|---|
| 0 510 826 A1 | 10/1992 | European Pat. Off. . |
| 0 577 423 A2 | 1/1994 | European Pat. Off. . |
| 0 576 835 A2 | 1/1994 | European Pat. Off. . |
| 0 605 254 A2 | 7/1994 | European Pat. Off. . |
| 2 162 782 | 2/1986 | United Kingdom . |

*Primary Examiner*—Glenn Dawson
*Attorney, Agent, or Firm*—Rosenblatt & Redano P.C.

[57] ABSTRACT

A hemostatic clip applicator system which is particularly useful for endoscopic procedures. A hemostatic clip applicator can be directly connected to a trigger assembly or indirectly connected to the trigger assembly through the use of an extension. The connection between the extension and the clip applicator is secured to prevent accidental release during the procedure. The applicator receives a longitudinal input and translates the input into relative component motion through the use of gearing to apply the clips.

19 Claims, 11 Drawing Sheets

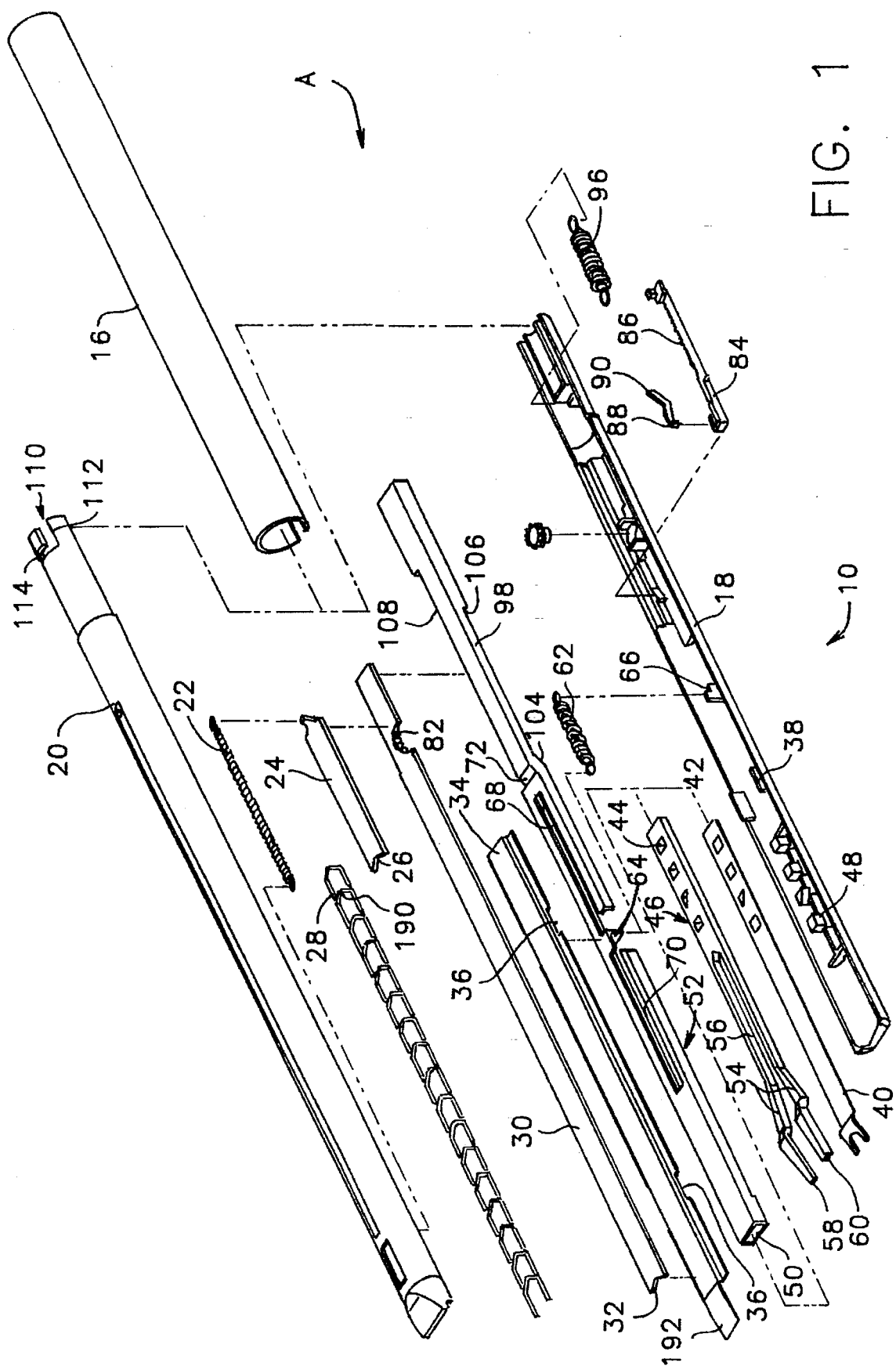

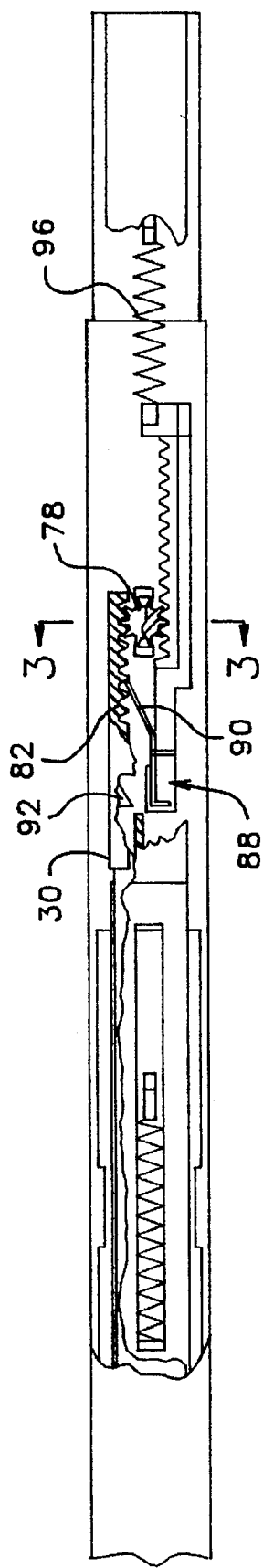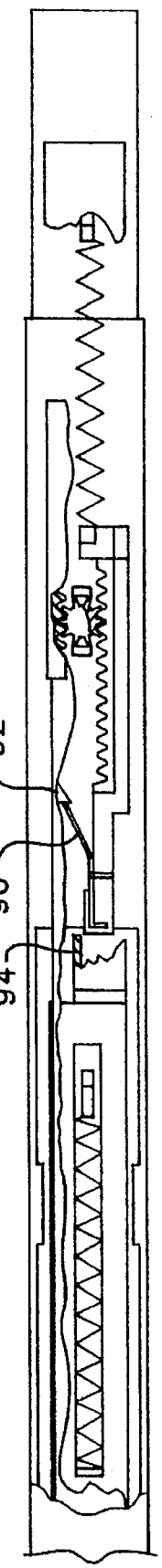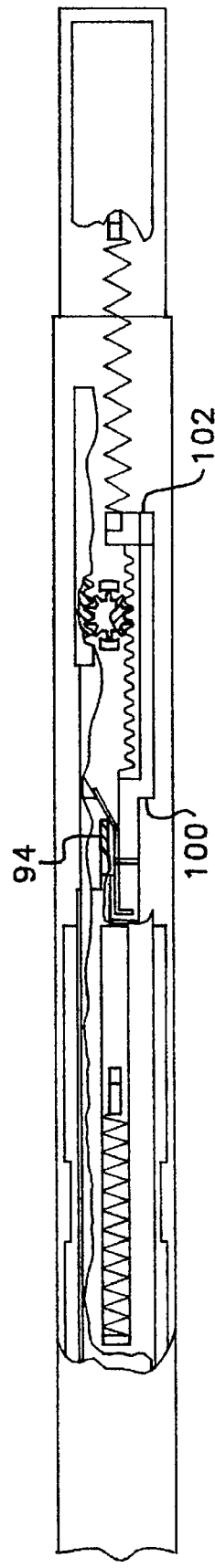

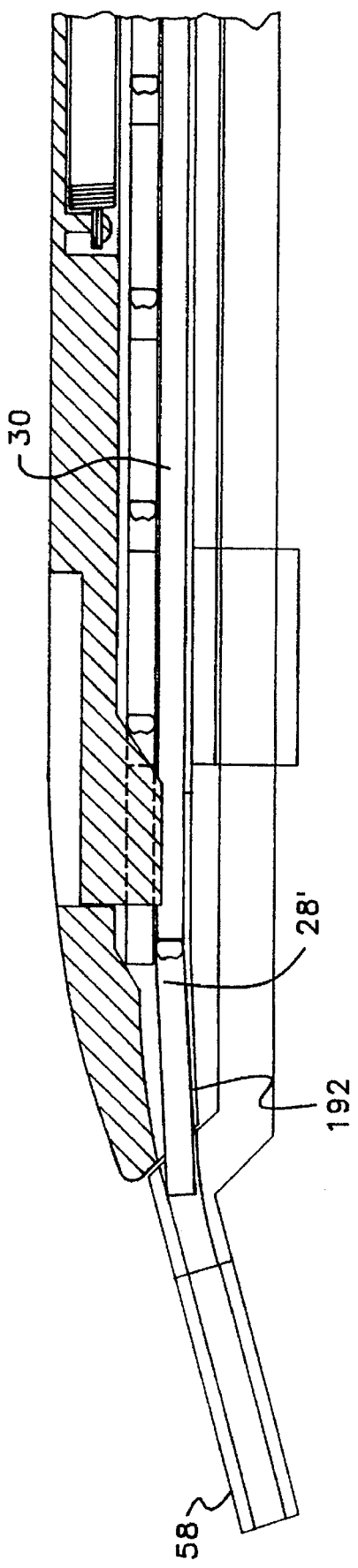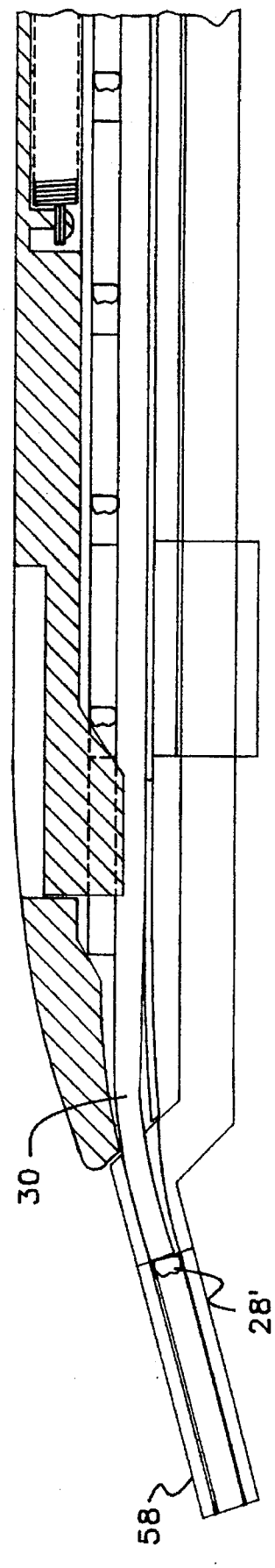
FIG. 4E
FIG. 4F

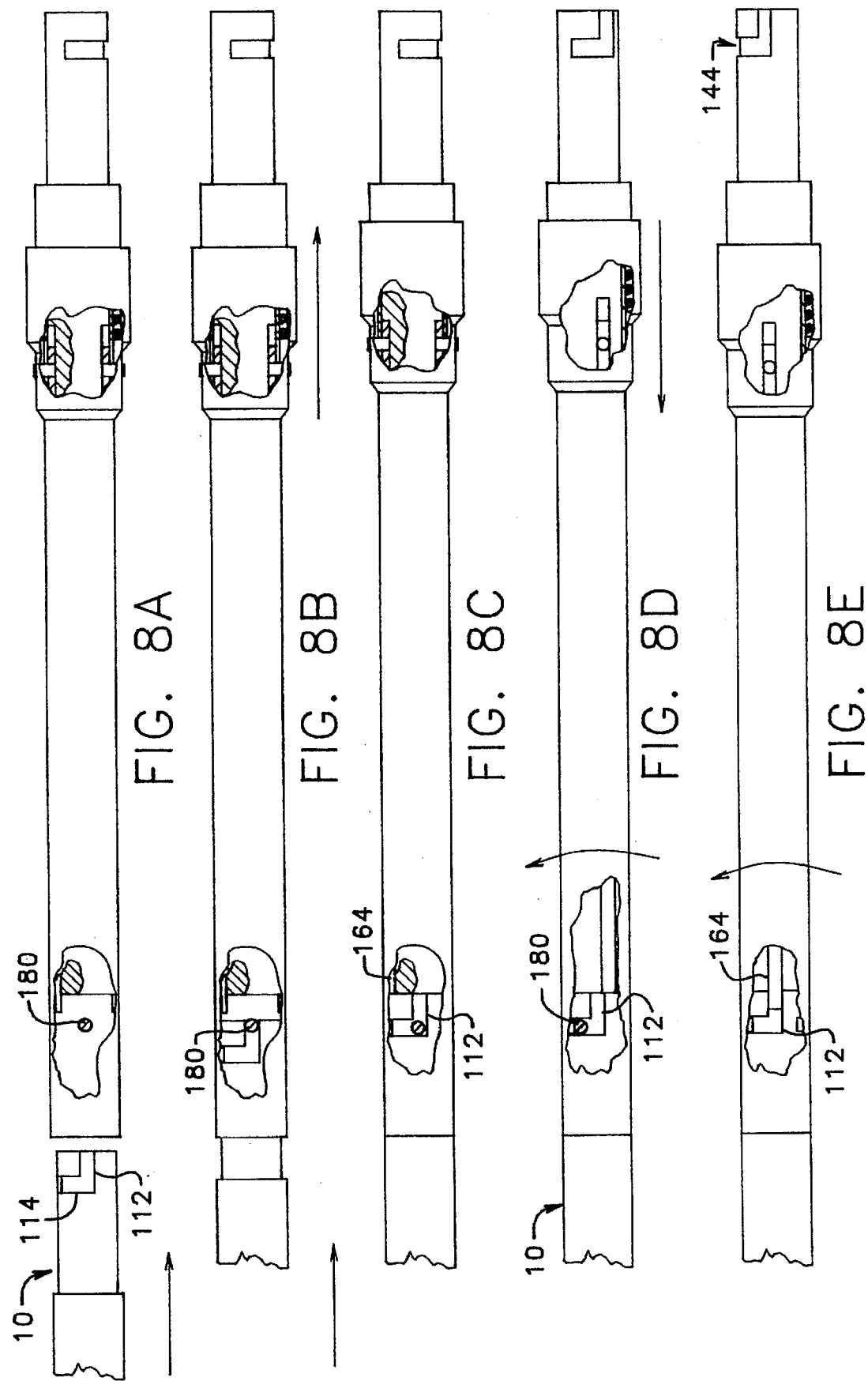

CLIP APPLICATOR SYSTEM

This is a continuation of application Ser. No. 07/999,437 filed on Dec. 31, 1992, now abandoned.

SPECIFICATION

1. Field of the Invention

The field of the invention relates to surgical instruments, more particularly those that can be used in endoscopic surgery with the emphasis on applying hemostatic clips.

2. Background of the Invention

Endoscopic surgery frequently requires the application of hemostatic clips or the use of other instruments which can ligate, grab or rip for a variety of purposes. Several significant characteristics of such instruments need to be simplicity in construction, reliability in operation, as well as low cost. Components that come into contact with internal organs in the body must also be effectively sterilized. Alternatively, the construction needs to be sufficiently economical to allow disposability of contaminated components. The layout of the instrument needs to be such as to give the surgeon good feedback during the procedure as to allow as much control as possible while using the instrument. If component systems are used, it is important to have them securely attached to each other to avoid disconnection during the procedure which could jeopardize the patient's condition should detachment occur during a procedure.

Surgical instruments that are adaptable to more than one procedure are preferred. A versatile system of surgical instruments which allows different types of instruments to be used in conjunction with a given actuating system is also a desirable feature.

In the past, various surgical instruments have been developed which address some, but not all of these needs. Some of the problems in addressing many of these needs is that a solution to one of such needs works at cross purposes to another. The result in the past has been fairly complex instruments which have adequately addressed one or two of such design requirements while compromising on the others. Hemostatic clip applicators of varying complexity are known in the art as exemplified by U.S. Pat. Nos. 5,049,152; 5,084,057; 5,100,420; 5,163,945; 4,496,090; 3,675,688; and Reissue 28,932. Some of these patents reveal the use of a trigger grip to actuate a rod which motion is transferred directly to an operating component for accomplishing the purpose the instrument. Typical of such devices is U.S. Pat. No. 4,759,364 which illustrates pincers that are rod actuated. Yet, other clip appliers use a scissor grip and linkage in combination with spring forces to accomplish the clip application. U.S. Pat. No. 5,104,395 illustrates this principle. Other clip applicators that work in a similar fashion employ a ratcheted counterwheel, wherein, every time a clip is applied, the wheel is rotated giving a visual display to the surgeon of the number of clips remaining. This type of clip applier is shown in U.S. Pat. No. 5,047,038. Alternatively, to a ratcheted wheel indicating the number of clips remaining, transparent covers, such as shown in U.S. Pat. No. 5,104,395 have also been used to allow the surgeon to see how many clips remain in the stack.

Outside the medical field, staplers have been used to hold objects together, such as in upholstery construction. Typical of such staplers is U.S. Pat. No. 2,296,493 illustrating a hand-operated stapling machine using a rack and pinion linkage with regard to the staple feeding operation.

The apparatus of the present invention has the objectives of providing a simple and economical construction that gives good feedback in the surgeon's hand as to the procedure being conducted. A system of components is provided which has reusable and disposable features. The connection system between the components gives certainty of fixation, thereby eliminating the risk of accidental disconnection during a procedure within the body. The system also provides for adjustability for using clips of various lengths or widths. The clip applicator also provides a feature to ensure sufficient jaw opening prior to feeding of the next successive clip. This avoids the hazards of jamming.

SUMMARY OF THE INVENTION

The hemostatic clip applicator system is particularly useful for endoscopic procedures. A hemostatic clip applicator can be directly connected to a trigger assembly or indirectly connected to the trigger assembly through the use of an extension. The connection between the extension and the clip applicator is secured to prevent accidental release during the procedure. The applicator receives a longitudinal input and translates the input into relative component motion through the use of gearing to apply the clips.

BRIEF DESCRIPTION OF THE DRAWINGS

FIG. 1 depicts is an exploded view showing the assembly of the components of the clip applicator.

FIGS. 2A–2C is a partial cutaway top view of the applicator as shown in FIG. 1 in a fully assembled condition and further illustrating the idler feature of the feeder.

FIGS. 4A–4F are sectional elevational views of the applicator with the feeder in various positions.

FIG. 8A shows the alignment of the applicator to the extension;

FIG. 8B shows insertion of the extension into the applicator;

FIG. 8C shows further extension of the extension over the applicator;

FIG. 8D illustrative relative rotation as between the applicator and the extension; and FIG. 8E shows the secured position between the applicator and the extension.

DETAILED DESCRIPTION OF THE PREFERRED EMBODIMENT

Figure 7:
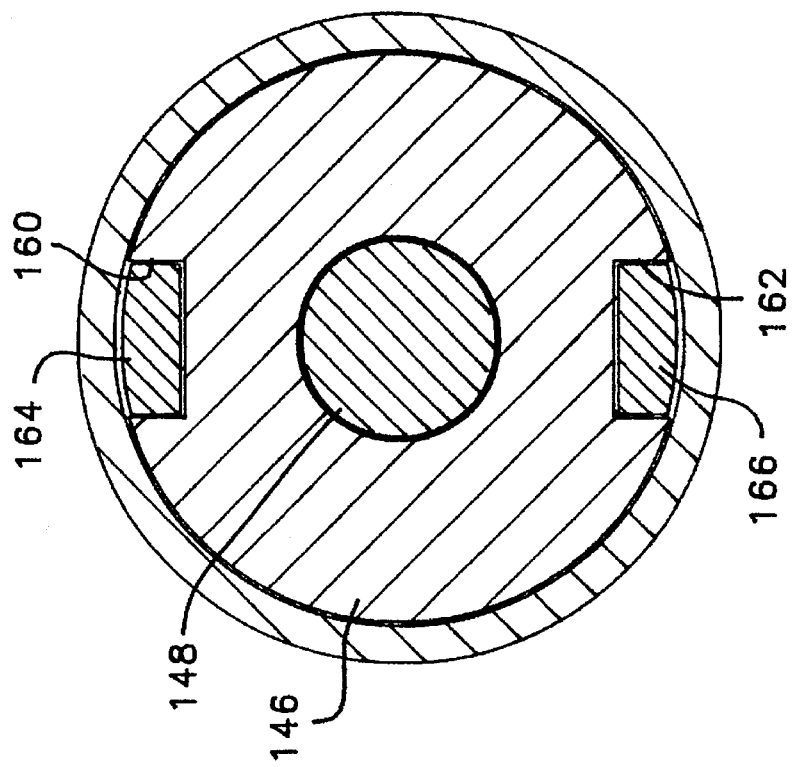
FIG. 7 is the view along section 7–7 shown in FIG. 6.

The apparatus A of the present invention is an instrument, or a variety of instruments, useful for endoscopic or less invasive surgeries. The major components in the preferred embodiment are a clip applicator generally referred to as 10 (see FIG. 1); an extension member 12 (see FIG. 5); and an actuator 14 (see FIG. 9). These components can be used altogether or, alternatively, the actuator 14 can be applied directly to the clip applicator 10. Alternatively, actuator 14 can be used with other types of surgical instruments which are operable by longitudinal input movement which creates a relative movement in response to an input force to accomplish a surgical procedure.

Referring now to FIG. 1, the details of the construction and operation of the clip applicator 10 will be described. A cover tube 16 holds bottom housing 18 and top cartridge 20 together. A pusher spring 22 is connected at its distal end to top cartridge 20 and at its proximal end to pusher 24. The proximal end of pusher 24 has a pushing surface 26 which is a surface conforming to the clip 28. In the preferred embodiment, a series of clips 28 can be stacked end-to-end in front of pushing surface 26; however, the scope of the invention is broad enough to include an applicator that applies one or more clips in sequence. The clips 28 rest on a feeder 30 as does pusher 24. The distal end of feeder 30 comprising a pushing surface 32 which, like pushing surface 26, conforms to the body shape of the clips 28 for the purpose of further advancing a clip as will be described below. The feeder 30 rests on cartridge floor 34. It should be noted that the assembly of the top cartridge 20, pusher spring 22, pusher 24, clips 28, feeder 30 and cartridge floor 34 can be assembled as a subassembly. The cartridge floor 34 has a plurality of cutouts 36 on both sides of its longitudinal centerline. A plurality of posts 38 conform to the shape of cutouts 36 and align the top cartridge 20 and the cartridge floor 34 to bottom housing 18.

Vessel stop 40 has a plurality of cutouts 42 which are aligned with cutouts 44 on jaw 46. Vessel stop 40 prevents vessel from dislodging clip 28. Jaw 46 and vessel stop 40 are put together by aligning openings 42 and 44 onto posts 48 in bottom housing 18 after initially slipping the assembly of vessel stop 40 and jaw 46 through the distal end 50 of closure member 52. Jaw 46 has a pair of opposed tapered surfaces 54 at the distal end of an elongated slot 56. Mounted distally to the tapered surfaces 54 are crimping members 58 and 60. Closure member 52 is mounted within housings 18 and 20 and can translate responsive to a force input. A spring 62 connected at its distal end to tab 64 on closure member 52 and on its proximal end to post 66 on bottom housing 18 applies a force in the proximal direction to closure member 52. Slot 68 on closure member 52 accommodates spring 62. Posts 48 in bottom housing 18 extend through openings 42 and 44 and into slot 70 on closure member 52, thereby, in the preferred embodiment, limiting the amount of travel of closure member 52 in the distal direction. While a transition 72 is illustrated to accommodate the placement of the floor 34 over the closure member 52, the apparatus A of the present invention encompasses a closure member that does not necessarily include such a transition surface 72.

Figure 3:
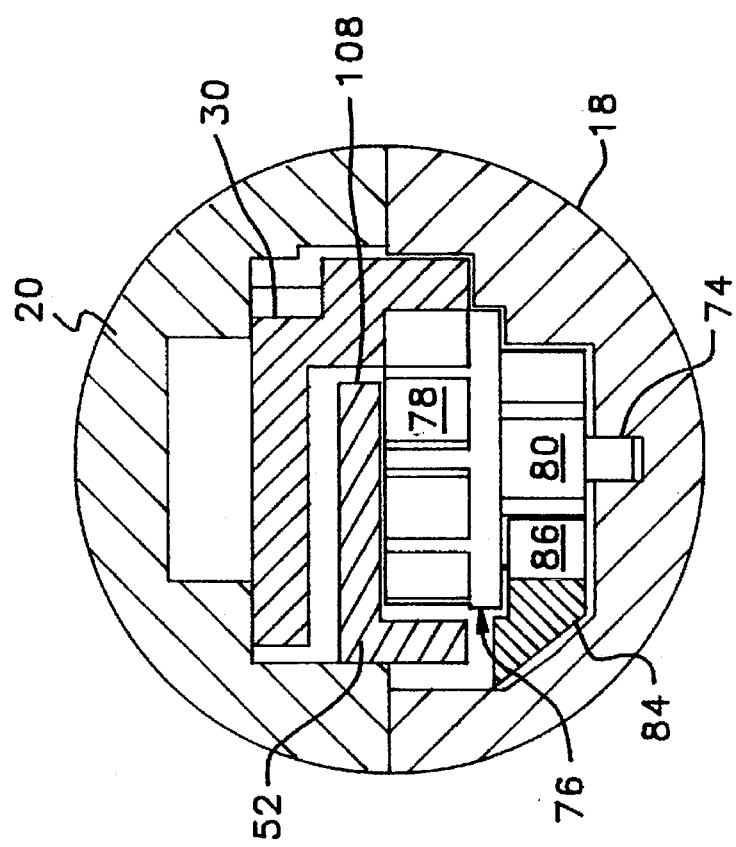
FIG. 3 is the view at section lines 3—3 shown in FIGS. 2A–2C.

Referring now to FIGS. 2A-2C and 3, bottom housing 18 accommodates spindle 74 of gear 76. Gear 76 is a compound gear, which, in the preferred embodiment, is really two gears parallel to each other supported by spindle 74. In the preferred embodiment, gear 76 has an upper gear 78 and a lower gear 80. The diameters and hence the number of teeth in gears 78 and 80 are different. The dictates of design determine the ratio of teeth and diameters of the gears 78 and 80 based on the degree of relative movement desired for the application. Different sized clips can be accommodated in the same applicator 10 by varying this ratio. While gears are recited, other motion reversing mechanisms are within the purview of the invention. This includes pulley systems as well as wheels that rely on friction to reverse motion, as well as lever assemblies. Spindle 74 may be motorized or powered to accomplish reverse motion as opposed to an input force to closure member 52 or to feeder 30 which are preferably stacked. Referring to FIGS. 1 and 2A-2C, it can be seen that feeder 30 has a plurality of teeth 82 which are visible in FIG. 1 due to a partial cutaway. Another view of teeth 82 is illustrated in FIGS. 2A-2C. As indicated in FIGS. 2A-2C, and 3, teeth 82 engage substantially in the same plane with upper gear 78. Lower gear 80 is substantially in the same plane as idler rack 84. Idler rack 84 has a plurality of teeth 86 which engage lower gear 80. As seen in FIGS. 1 and 3, teeth 82 face teeth 86 on opposite sides of longitudinal axis of cover tube 16 with teeth 82 being in a higher plane than teeth 86 of idler rack 84. Mounted to the distal end of idler rack 84 is rack latch 88. Rack latch 88 has a cantilevered and inclined finger 90. As shown in FIGS. 2A-2C, finger 90 extends obliquely toward teeth 82 but is in a plane below such teeth such that upon distal movement of closure member 52, finger 90 skips over tab 92 as shown by comparing the top two views of FIGS. 2A-2C. When the closure member 52 moves in the proximal direction, a tab 94, which extends downwardly from the closure member parallel to its longitudinal axis, engages finger 90 and moves it up and over tab 92. The proximal end of idler rack 84 is connected to spring 96 with the proximal end of spring 96 secured to the bottom housing 18, as shown in FIG. 1. The underside of closure member 52 has a notched area 98, as shown in FIG. 1. Idler rack 84 has a shoulder 100 and an opposed shoulder 102. The notched area 98 in closure member 52 is defined by shoulders 104 and 106 (see FIG. 1). The distance between shoulders 100 and 102 is smaller than the distance between shoulders 104 and 106 for a purpose which will be described below. Closure member 52 has a notched surface 108 to accommodate the feeder 30, as shown in the section view of FIG. 3.

Figure 9:
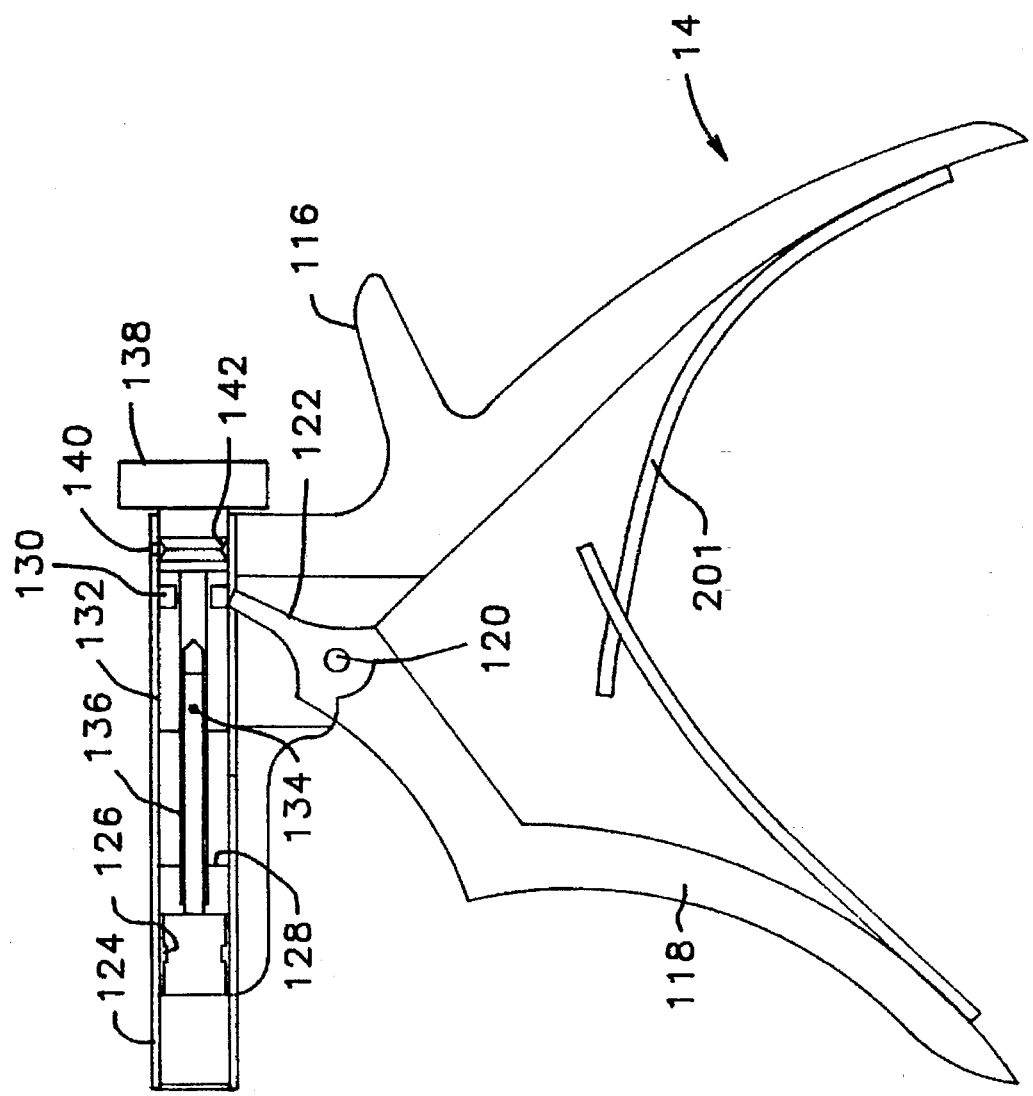
FIG. 9 is the operating mechanism in an open position.
Figure 10:
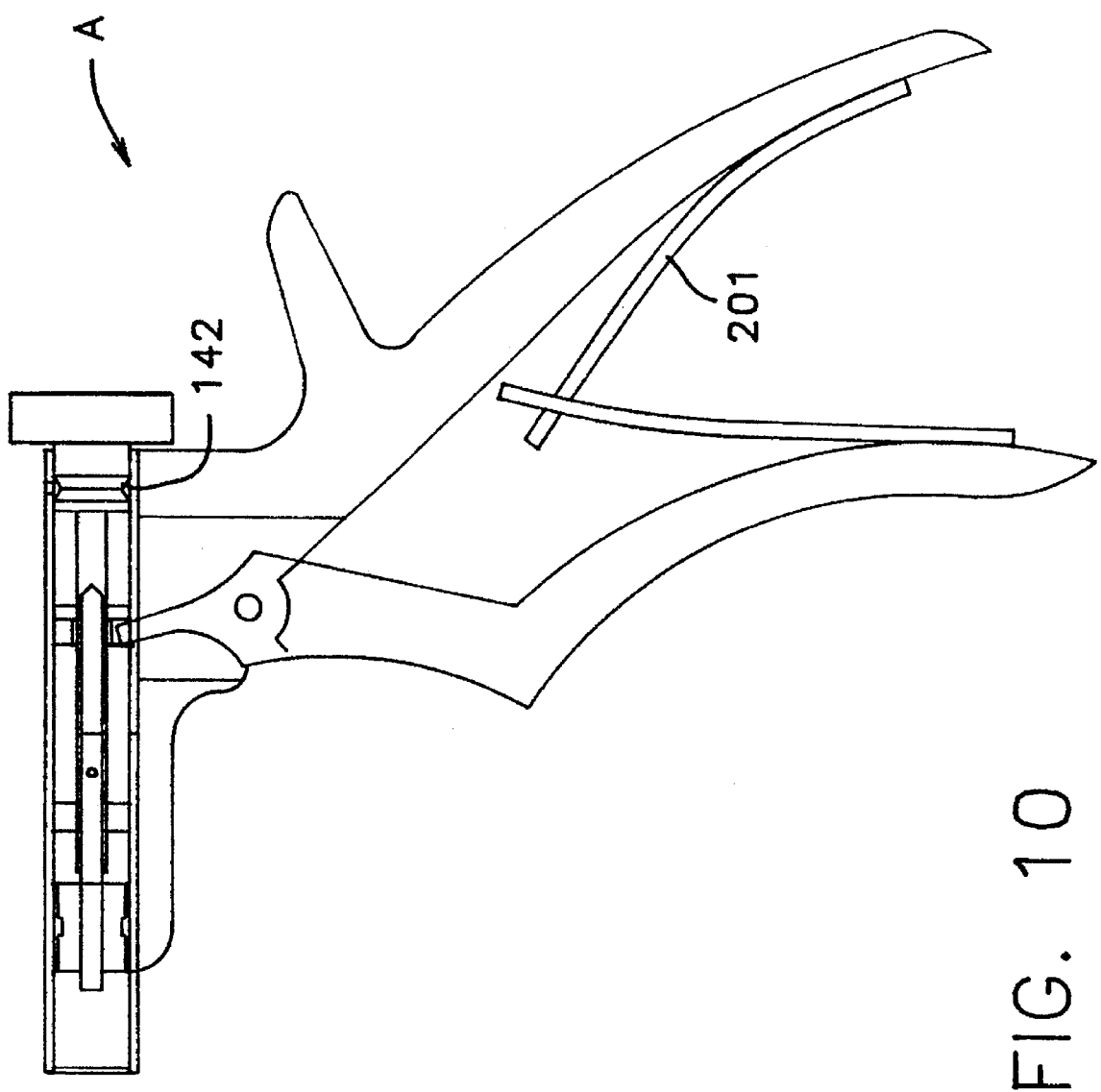
FIG. 10 is the operating mechanism in a closed position.

The operation of the clip applicator 10 is initiated by a force supplied to closure member 52. Prior to getting into the details of the operation of clip applicator 10, the operation of the extension member 12 and actuator 14 will be described. FIG. 1 illustrates that the top cartridge 20 has an L shaped slot 110, which has a longitudinal component 112 and a radial component 114. While only one L shaped slot is shown in FIG. 1, those skilled in the art can appreciate that a plurality of such L shaped slots 110 can be employed for the purposes of securing the clip applicator 10 either to the extension member 12 or the actuator 14. The actuator 14 in its two positions is illustrated in FIGS. 9 and 10. A handle 116 is mounted to a trigger 118 at pin 120. Trigger 118 has an extension tab 122 which extends into barrel 124. At least one pin 126 extends into barrel 124 and holder 128. Pin or pins 126 are mounted into a position so as to engage L shaped slot 110 (see FIG. 1) of top cartridge 20. Through a bayonet-type mounting, the clip applicator 10 is longitudinally inserted so that longitudinal component 112 of L shaped slot 110 passes by pin or pins 126. The clip applicator 10 is then rotated to move the radial component 114 of L shaped slot 110 past pin or pins 126 to secure the attachment. It should be noted that there is a pin 126 for each L shaped slot 110 provided in top cartridge 120.

Tab 122 extends into barrel 124 and engages a groove 130 on sleeve 132. A dowel 134 fixes rod 136 to sleeve 132. A knob 138 is rotatably mounted on its central axis to barrel 124 and is retained against longitudinal movements by virtue of pin 140 extending into groove 142 of sleeve 132. When the clip applicator 10 is inserted into barrel 124 and engaged on pins 126, rod 136 is aligned with closure member 52. As a result, moving the trigger from the position shown in FIG. 9 to the position shown in FIG. 10, translates sleeve 132 and rod 136 distally, which, in turn, begins distal movement of closure member 52. It should be noted that the connection, as illustrated in FIGS. 9 and 10, is not a fail-safe connection in the sense that rotation of the clip applicator 10 can result in disengagement from actuator 14. However, without the use of extension member 12, the procedure being done with the clip applicator 10 connected directly to the actuator 14 is primarily not very deep within the body of the patient; therefore, making the security of the attachment a lesser concern than in a situation involving an endoscopic procedure. However, the connection, as previously described, at the distal end of barrel 124 involving pins 126 can be fashioned differently along the lines as will be described with reference to FIGS. 5–7 so as to provide a fail-safe connection if the clip applicator 10 is connected directly to the actuator 14.

It should be noted that the trigger 118 returns from its closed position shown in FIG. 10 to its open position shown in FIG. 9 by virtue of spring 201.

Figure 5:
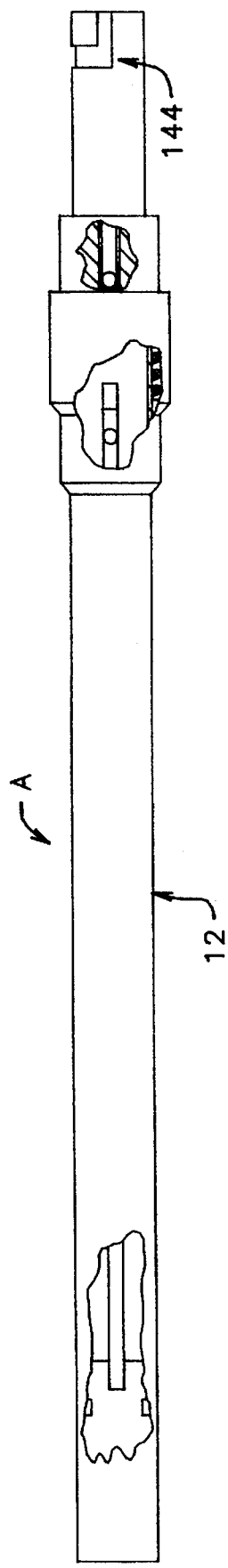
FIG. 5 illustrates the extension member with a partial cutaway showing its operation.
Figure 6:
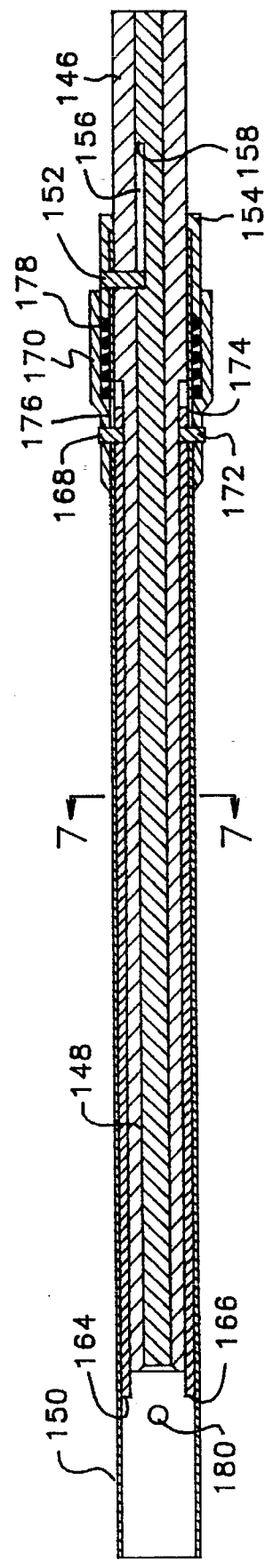
FIG. 6 is a section view of the extension member of FIG. 5.

At times it may be desirable to use the apparatus A of the present invention in an endoscopic procedure. When doing so, the extension member 12 becomes an additional advantage. Referring to FIG. 5, the outer assembly of the extension member 12 is illustrated. An L shaped slot 144 is at the proximal end of extension member 12 and is for the same purpose as previously described in L shaped slot 110. L shaped slot 144 is disposed in guide 146 which extends the substantial length of extension member 12. Concentrically mounted to guide 146 is extension rod 148. Also, concentrically mounted with respect to guide 146 is tube 150. Tube 150 is secured to guide 146 by pin 152 which extends radially through guide 146, tube 150, and fixed cuff 154. Extension rod 148 has a longitudinal slot 156 to allow extension rod 148 to translate with respect to pin 152 with pin 152 being a distal travel stop as shoulder 158 engages pin 152. The position of extension rod 148 corresponds to the open position of actuator 14, as shown in FIG. 9. When the actuator 14 is assembled to the extension member 12, rod 136 and extension rod 148 are in alignment for tandem movement. As shown in FIG. 7, guide 146 has a pair of opposed slots 160 and 162. Slides 164 and 166 are disposed in slots 160 and 162, respectively. A pin 168 extends through slide cuff 170 and into slide 164. Similarly, a pin 172 extends through slide cuff 170 and into slide 166. It should be noted that the tube 150 has slots 174 and 176 to allow the assembly of slide cuff 170 and slides 164 and 166 to move with respect to guide 146. A spring 178 biases slide cuff 170 distally as a result of it bearing on fixed cuff 154. One pin 180 for each L shaped slot 110 mounted to clip applicator 10 is disposed at the distal end of extension member 12.

The L shaped slots 110 on the clip applicator 10 are preferably identical to the L shaped slots on the extension 12 for interchangeability with actuator 14. Likewise, the pins 180 on extension 12 are preferably identical to pins 126 on the actuator 14.

All of the components of extension member 12 having been described, the method of securing the clip applicator 10 will now be described. As shown in FIGS. 8A–8E, the longitudinal component 112 of L shaped slot 110 is aligned with pin 180. The clip applicator 10 is advanced proximally until longitudinal slot 112 registers with pin 180, as shown as the second step in the sequence of motions in FIG. 8. The next step requires further advancement of clip applicator 10 in the proximal direction until pin 180 bottoms in longitudinal slot 112. As the third step occurs, the slides 164 and 166 are pushed proximally from their position in the second step, which, in turn, translates slide cuff 170 and compresses spring 178. In the fourth step, the applicator 10 is rotated so that radial component 114 of L shaped slot 110 moves past pin 180. As the rotation progresses, ultimately the longitudinal component 112 becomes aligned with a corresponding slide 164 or 166. At that time, the force of spring 178 acts on slide cuff 170, which, through pins 168 and 172, forces slides 164 and 166 distally until they are registered in longitudinal component 112. The force of spring 178 then retains the connection between extension member 12 and applicator 10 such that rotation is prevented and there is no accidental disconnection. If disconnection is desired, a force in the proximal direction must be applied to slide cuff 170 to overcome the force of spring 178 and translate slides 164 and 166 proximally to take them out of register with longitudinal component 112 of L shaped slot 110. At that time, rotation in the opposite direction of the previous rotation reverses the steps shown in FIGS. 8A–8E and allows for disconnection between the extension member 12 and the clip applicator 10. The extension member 12 can be made of any desirable materials and, as previously stated, may have a similar connection at its proximal end, as illustrated for its distal end. This type of fail-safe connection could be positioned on the proximal end of extension member 12 in lieu of L shaped slot 144. Accordingly, depending on the need, a fail-safe connection can be provided in the connection between the actuator 14 and the extension member 12, as well as between the extension member 12 and the clip applicator 10 and between the actuator 14 and the clip applicator 10.

Those skilled in the art will appreciate that the actuator 14 is reusable as can be extension member 12.

It should be noted that during the procedure, the surgeon can reorient the position of crimping members 58 and 60 (see FIG. 1) by applying a rotational force to knob 138 (see FIG. 9). A rotational force applied to knob 138 is transmitted through sleeve 132, dowel 134, into holder 128 and pins 126, which causes the clip applicator 10, or the combination of clip applicator 10 and extension member 12, to rotate in response to rotation of knob 138.

Referring now to FIGS. 1–4, the operation of the clip applicator 10 will now be described in detail. The process of positioning and feeding the clips 28 will be described by reference to FIGS. 4A–4F. In FIG. 4A, the feeder 30 is distally extended so that a clip 28 is between crimping members 58 and 60. Since the views of FIGS. 4A–4F are in sections, only crimping member 58 is illustrated. In the second step illustrated in FIG. 4B, the feeder 30 has been retracted thus allowing the pusher 24 (see FIG. 1) to push the clip stack 28 forward moving the next clip in line 28' through the intermediate position (as shown in dashed lines) and final position illustrated in FIG. 4B. The pusher 24 pushes clip 28' into the delta point 182. The delta point 182 has a ramp surface 184. The top cartridge 20 has a ramp surface 186. The front end or legs 188 of clip 28' engage ramp surface 186. The first contact is made between legs 188 and ramp surface 186. After this first contact is made, the next clip in line 28' is rotated slightly before the inner apex 190 (see FIG. 1) of clip 28' contacts sloped surface 184. The next step as illustrated in FIG. 4C where the clip 28' is now in position to be fed between crimping members 58 and 60. The next step as shown in FIG. 4D where the feeder 30 is pushing the clip 28' distally. The next step is illustrated in FIG. 4E where clip 28' enters between crimping members 58 and 60.

Figure 4A:
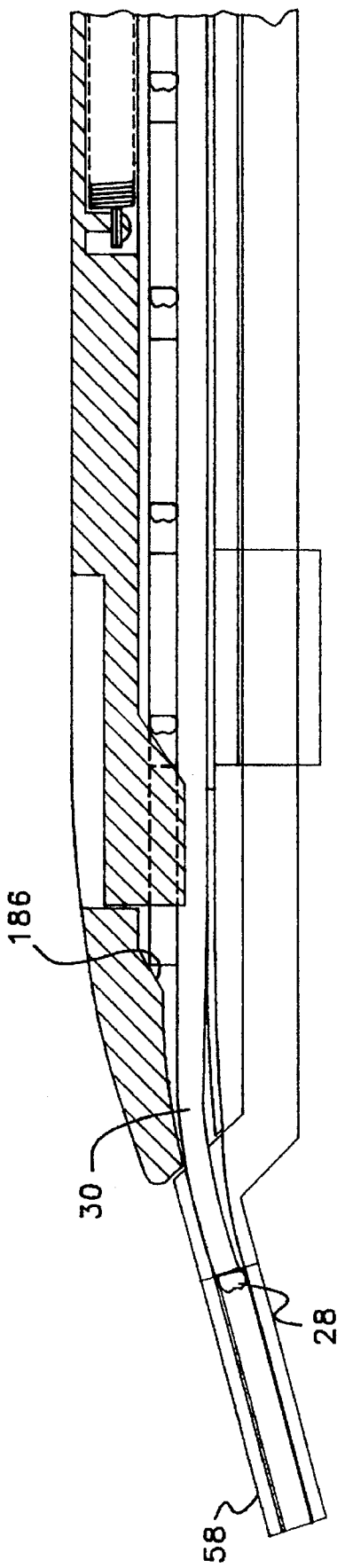
Figure 4B:
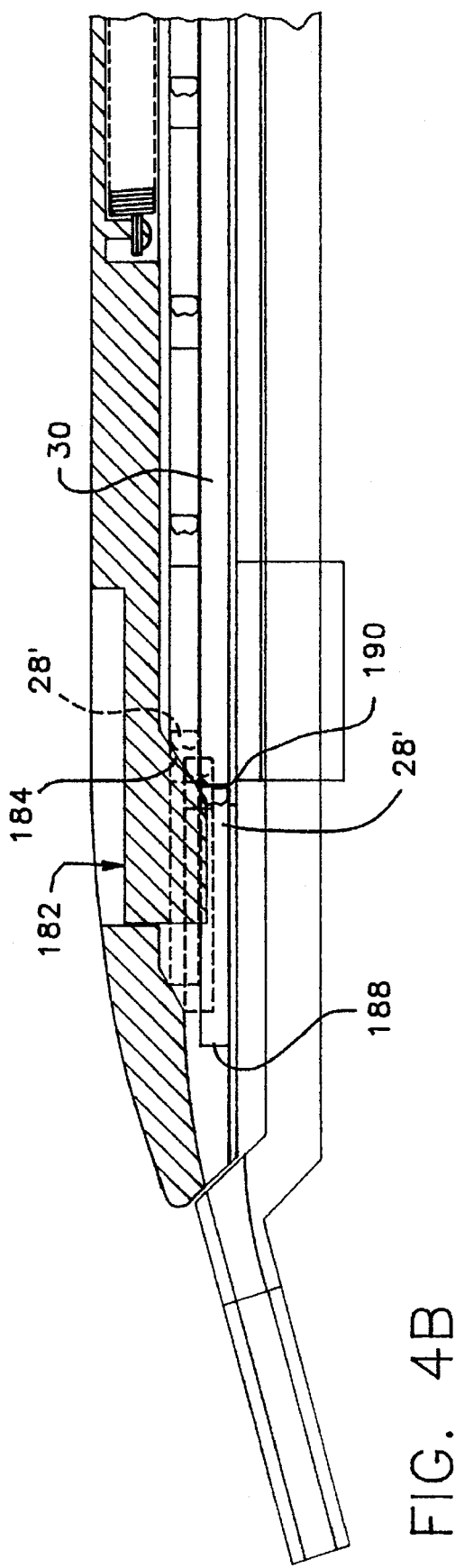
Figure 4C:
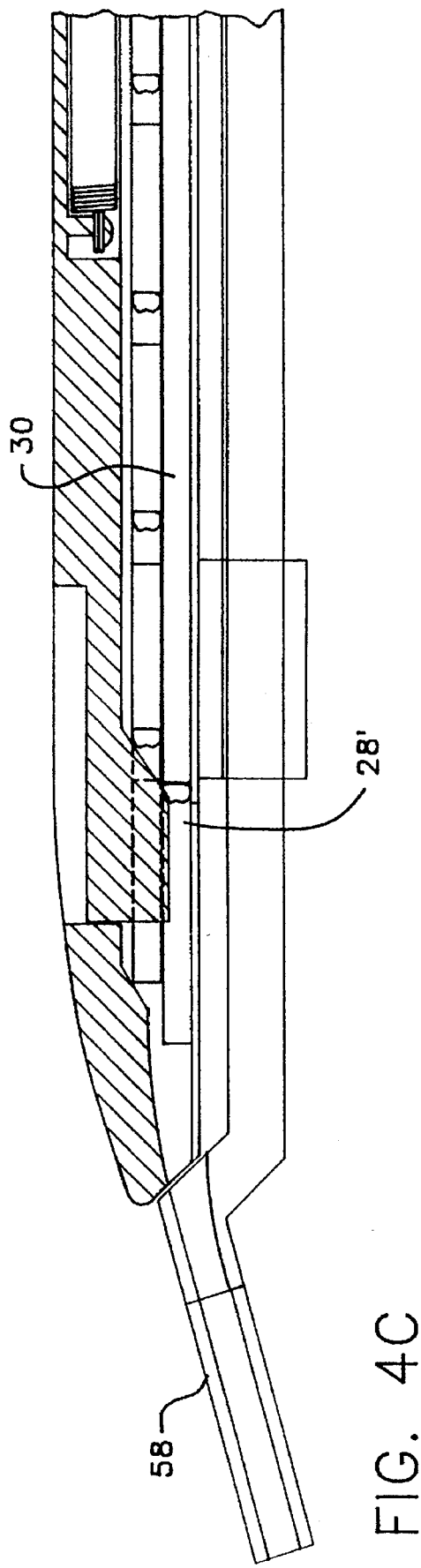

Referring now to FIG. 1, it will be seen that the cartridge floor 34 has a flexible distal segment 192. The flexibility of the cartridge floor 34 gives the clip 28' the ability to rotate into approximately a 15° angle. FIG. 4F indicates the position shown in FIGS. 4A–4F with clip 28' now ready for application.

To obtain the motions previously described with reference to FIG. 4, FIGS. 1, 2A–2C, and 9 must be reviewed. The same sequence occurs if extension 12 is mounted to actuator 14. Moving the trigger 118 from the open position of FIG. 9 into the closed position of FIG. 10 advances rod 136 which, in turn, advances rod 148, which provides a distal pushing force on closure member 52. Closure member 52 begins to move distally. As a result of such distal movement, shoulder 106 (see FIGS. 2A–2C) of closure member 52 (or first member) engages shoulder 102 on rack 84 (see FIG. 1). Thereafter, closure member 52 and idler rack 84 move in tandem. As the idler rack 84 advances, it rotates lower gear 80 (a part of the rotating assembly) as a result of the engagement of gear 80 with teeth 86 on idler rack 84. Gear 76 then rotates through the connection between upper gear 78 and teeth 82 on feeder 30 (or second member), causing feeder 30 to move in the proximal direction, as seen by comparing FIGS. 4A to 4B. Simultaneously, while the feeder is being retracted, the closure member 52 is advancing toward tapered surfaces 54. The clip 28, which was between jaws 58 and 60 is crimped as jaws 58 and 60 move toward each other when distal end 50 of closure member 52 advances against ramped surfaces 54 pushing them together. It should be noted that the feeder 30 has retracted sufficiently out of position between crimping members 58 and 60 before members 58 and 60 start moving toward each other. The sequence of these movements can be facilitated by selective placement and angularity of ramp surfaces 54 on jaw 46.

Figure 4D:
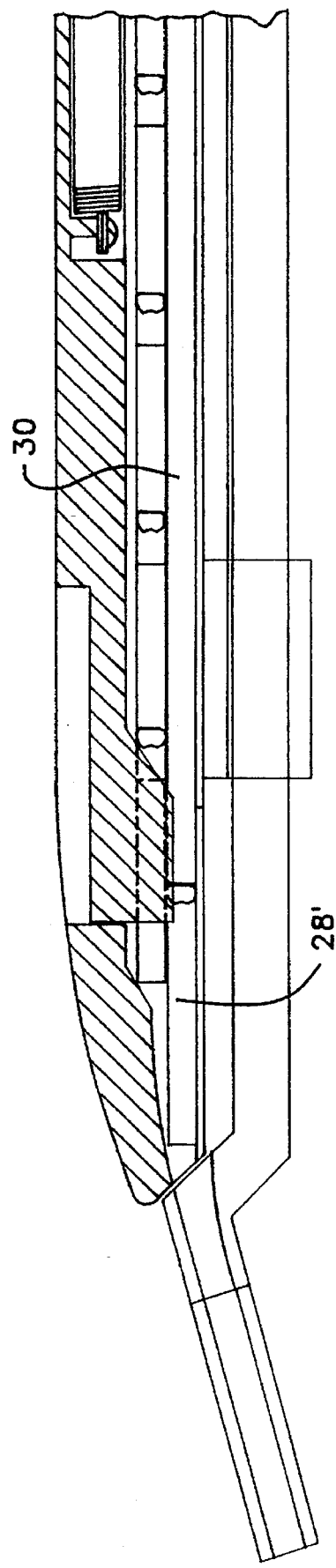

As has been explained, the operation of actuator 14 results in crimping of clip 28 as closure member 52 advances distally over jaw 46. As this is occurring, the idler rack 84 moves distally as well, allowing finger 90 to snap over tab 92, as shown in FIGS. 2A–2B, by comparing the first and second positions. With the closure member 52 fully advanced distally, the trigger 118 can be released. Spring 62 urges closure member 52 proximally allowing the crimping members 58 and 60 to spread apart. Idler rack 84 moves proximally with closure member 52 in the proximal direction until finger 90 abuts tab 92. At that point, closure member 52 can continue to move proximally due to notched area 98 being longer than the distance between shoulders 100 and 102 of idler rack 84. However, once the finger 90 hits tab 92, idler rack 84 is immobilized preventing any further distal movement of the feeder 30. The closure member 52 continues to move proximally until tab 94 engages finger 90, as shown in FIG. 2C. The continuing proximal movement of closure member 52 forces finger 90 around tab 92. When this occurs, spring 96 vigorously pulls idler rack 84 proximally until shoulder 102 contacts shoulder 106 on the closure member 52 (see FIG. 1). The sudden proximal movement of idler rack 84 turns gear 76 vigorously resulting in rapid distal movement of feeder 30, as illustrated in FIG. 4D–4F. At that point, the next clip 28' is ready for application. The purpose of temporarily immobilizing idler rack 84 is to allow the closure member to retreat proximally a sufficient amount to allow the crimping members 58 and 60 to spread sufficiently before the feeder 30 advances the next clip 28' to position between crimping members 58 and 60. Without such a delay, a possibility of jamming could exist if the feeder 30 advances the next clip 28' prior to the crimping members 58 and 60 having had an opportunity to spread far enough to accept the next clip 28'.

Figure 11A:
FIG. 11A illustrates a partial cutaway view of an alternative embodiment of a stapler showing a formed staple.
Figure 11B:
FIG. 11B is the stapler of FIG. 11A in a different position with the staple ejected.
Figure 11C:
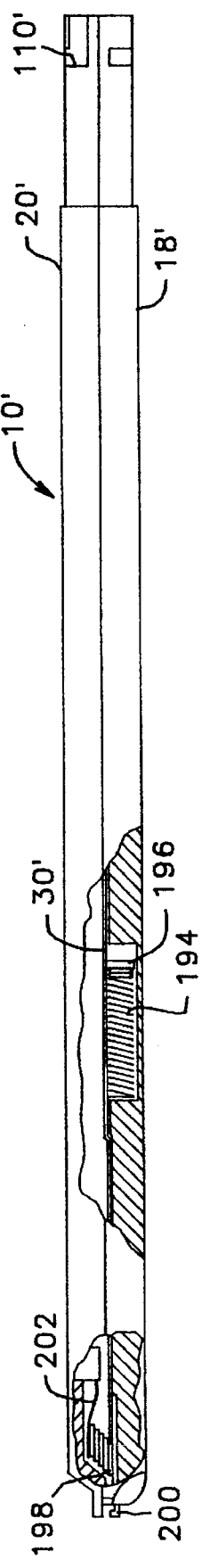
FIG. 11C is an elevational view of the alternative embodiment shown in FIG. 11A in partial cutaway.

FIGS. 11A–11C illustrates a stapler 10' which can be connected to the actuator 14 or the extension member 12 in the manner previously described. In the embodiment illustrated in FIGS. 11A–11C, an L shaped slot 110' is used in the manner previously described. A feeder 30' is mounted for reciprocal movement within a top cartridge housing 20' and a bottom housing 18'. A return spring 194 is mounted to the bottom housing 18' and bears on tab 196 to bias the feeder 30' in the proximal direction. The feeder 30' is actuated in a distal direction by using an actuator 14, which causes rod 136 to contact the feeder 30' in the manner previously described to move the feeder 30' distally advancing a staple 198 toward anvil 200. The staple 198 is formed around anvil 200 due to the advancement of feeder 30'. Upon release of the trigger 118, spring 194 pushes proximally on tab 196 which causes feeder 30' to move proximally. At that point, pusher 202 pushes the next staple in line downwardly into the forming path so that upon subsequent distal movement of feeder 30', the entire process is repeated.

The foregoing disclosure and description of the invention are illustrative and explanatory thereof, and various changes in the size, shape and materials, as well as in the details of the illustrated construction, may be made without departing from the spirit of the invention.

What is claimed is:

1. A surgical instrument, comprising:

a handle component;

a cartridge component comprising an elongated tubular body;

said handle component comprising an actuating member mounted therein for selective reciprocal proximal and distal movements along a longitudinal axis thereof;

said body having a longitudinal axis, and further comprising:

a clip feeder;

a closure member;

said clip feeder connected to said closure member by a direction reversing mechanism at a first location within said body for selective movements so that when said clip feeder moves in a first direction, said closure member can move in a second direction which is opposite said first direction;

one of said feeder and said clip closure member separately connected to said actuating member, which when said one of said clip feeder and said closure member moves in a first direction results in the other of said clip feeder and closure member which is not connected to said actuator member moving in an opposite direction from said first direction by virtue of said direction reversing mechanism, for feeding and forming clips.

2. The instrument of claim 1, wherein:

said cartridge component is selectively disengageable from said handle component.

3. The instrument of claim 2, wherein:

said actuating member releasably engages one of said clip feeder or said closure member as a direct result of securing said cartridge component to said handle component.

4. The instrument of claim 3, wherein said direction reversing mechanism further comprises:

a connection which converts linear motion of one of one of said clip feeder and said closure member into reverse linear motion of the other of said clip feeder and said closure member through the use of at least one interconnecting rotating member.

5. The instrument of claim 4, wherein:

said interconnecting rotating member comprises at least one rounded member rotating in at least one plane to connect said closure member and said clip feeder for opposed movement.

6. The instrument of claim 5, wherein said interconnecting rotating member further comprises:

at least two rounded members rotating in different planes on the same axis, where one rounded member is connected to said clip feeder and the other to said closure member.

7. The instrument of claim 6, wherein:

said rounded members have different diameters for producing different opposed movement of said clip feeder and said closure member.

8. The instrument of claim 7, wherein:

the cartridge component can at different times be used to accommodate clips requiring different amounts of said opposed movement, by selective variation in the relative dimensions between said rounded members for each such occasion.

9. The instrument of claim 5, wherein:

said interconnecting rotating member comprises at least one gear;

at least one rack disposed on one of said clip feeder and said closure member which meshes with said gear for reverse motion between said clip feeder and said closure member.

10. The instrument of claim 9, wherein:

said clip feeder and said closure member are stacked in said cartridge component;

said clip feeder and said closure member each comprising a rack, said racks facing each other in parallel planes;

said interconnecting rotating member comprises a single spindle on which a plurality of said at least one gear are concentrically mounted, said spindle extending transversely to said parallel planes.

11. The instrument of claim 2, wherein:

said handle component and said cartridge component forming a connection which can be formed and released by virtue of a plurality of movements of said cartridge component in different planes.

12. The instrument of claim 11, wherein:

said cartridge component is selectively engageable and disengageable from said handle component by a combination of a linear movement relative to said handle component along said longitudinal axis and a rotational movement relative to said handle component.

13. The instrument of claim 1, wherein said direction reversing mechanism further comprises:

a connection which converts linear motion of one of said clip feeder and said closure member into reverse linear motion of the other of said clip feeder and said closure member through the use of at least one interconnecting rotating member.

14. The instrument of claim 13, wherein:

said interconnecting rotating member comprises at least one rounded member rotating in at least one plane to connect said closure member and said clip feeder for opposed movement.

15. The instrument of claim 14, wherein said interconnecting rotating member further comprises:

at least two rounded members rotating in different planes on the same axis, where one rounded member is connected to said clip feeder and the other to said closure member.

16. The instrument of claim 15, wherein:

said rounded members have different diameters for producing different opposed movement of said clip feeder and said closure member.

17. The instrument of claim 16, wherein:

the same cartridge component can at different times be used to accommodate clips requiring different amounts of said opposed movement, by selective variation in the relative dimensions between said rounded members for each such occasion.

18. The instrument of claim 16, wherein:

said interconnecting rotating member comprises at least one gear;

at least one rack disposed on one of said clip feeder and said closure member which meshes with said gear for reverse motion between said clip feeder and said closure member.

19. The instrument of claim 18, wherein:

said clip feeder and said closure member are stacked in said cartridge component;

said clip feeder and said closure member each comprising a rack, said racks facing each other in parallel planes;

said interconnecting rotating member comprises a single spindle on which a plurality of said at least one gear are concentrically mounted, said spindle extending transversely to said parallel planes.

* * * * *